US008398652B2

(12) United States Patent
Ritchey et al.

(10) Patent No.: US 8,398,652 B2
(45) Date of Patent: Mar. 19, 2013

(54) EAR TAG INSTALLATION TOOL AND METHOD

(75) Inventors: Eugene B. Ritchey, Brighton, CO (US);
Craig E. Ritchey, Brighton, CO (US);
Grant A. Ritchey, Hudson, CO (US)

(73) Assignee: Ritchey Manufacturing, Inc., Brighton, CO (US)

( * ) Notice: Subject to any disclaimer, the term of this patent is extended or adjusted under 35 U.S.C. 154(b) by 185 days.

(21) Appl. No.: 12/770,320

(22) Filed: Apr. 29, 2010

(65) Prior Publication Data
US 2011/0270266 A1 Nov. 3, 2011

(51) Int. Cl.
*A61B 17/00* (2006.01)
(52) U.S. Cl. .......................................... 606/117; 40/301
(58) Field of Classification Search .................. 606/116,
606/117, 184, 185, 188, 167, 205–211, 187,
606/181, 142, 143; 40/300, 301; 81/415,
81/419, 421, 411, 478, 783, 472; 119/655;
D30/155; 227/144, 142, 143, 77, 148–150,
227/141, 153, 67, 68, 27, 107, 108, 152,
227/30, 35, 34; 600/564, 567; 30/154, 155,
30/162; 63/12; 407/72, 73, 84, 88–90, 101,
407/102, 36; 83/83, 658, 544, 467.1, 455,
83/440.1, 440.2, 571, 839; 604/47
See application file for complete search history.

(56) References Cited

U.S. PATENT DOCUMENTS

| 630,349 A | 8/1899 | Harvey |
| 982,896 A | 1/1911 | Stoll |
| 1,347,868 A | 7/1920 | Nichols |
| 1,479,512 A * | 1/1924 | Perkins ........................... 227/77 |
| 2,625,760 A | 1/1953 | Cleal |
| 3,214,856 A | 11/1965 | Brierley |

(Continued)

FOREIGN PATENT DOCUMENTS

| BE | 1006747 | 11/1994 |
| CA | 2170320 | 8/1996 |

(Continued)

OTHER PUBLICATIONS

U.S. Appl. No. 29/045,567, filed Oct. 24, 1995, Ritchey.

(Continued)

*Primary Examiner* — Kathleen Holwerda
*Assistant Examiner* — Jocelin Tanner
(74) *Attorney, Agent, or Firm* — Sheridan Ross PC

(57) ABSTRACT

An apparatus and method of installing livestock ear tags are provided. The apparatus includes handle members that control the insertion of a piercing needle that cuts an opening through an animal's ear. A slidable head assembly enables efficient manipulation of the piercing needle and reload of a new piercing needle for installing another tag. The piercing needle has attached to it a securing tab of the ear tag. The tab is stripped from the piercing needle after the needle clears the far side of the ear thereby securing the tag to the ear by placing the tab on the opposite side of the ear. The piercing needle is preferably disposable. The piercing needle has an integral tissue capturing cavity for capturing a slug of tissue from the animal's ear as the needle passes through the ear. The tissue sample can be used for subsequent animal health testing. The piercing needle is automatically captured by the tool after installation to prevent contamination of the tissue sample by release of the needle onto the ground.

11 Claims, 4 Drawing Sheets

U.S. PATENT DOCUMENTS

| | | | |
|---|---|---|---|
| D204,238 S | 4/1966 | Dumbrell | |
| 3,526,987 A | 9/1970 | McCarty et al. | |
| 3,552,051 A | 1/1971 | Ritchey | |
| 3,595,201 A | 7/1971 | Oudenhoven | |
| 3,675,357 A | 7/1972 | Magee | |
| 3,731,414 A | 5/1973 | Murphy et al. | |
| 3,756,200 A | 9/1973 | Ohlhausen | |
| D229,571 S | 12/1973 | Fearing | |
| 3,826,030 A | 7/1974 | Read | |
| 3,850,360 A | 11/1974 | Ritchey | |
| 3,867,777 A | 2/1975 | Potter | |
| 3,900,925 A | 8/1975 | La Torraca | |
| 3,916,904 A | 11/1975 | Ritchey | |
| 3,949,708 A | 4/1976 | Meeks | |
| 3,959,908 A | 6/1976 | Lowe | |
| D241,558 S | 9/1976 | Schwindt et al. | |
| 4,000,744 A | 1/1977 | Ritchey | |
| 4,021,952 A | 5/1977 | Brierley | |
| 4,059,074 A | 11/1977 | Furer et al. | |
| 4,121,591 A | 10/1978 | Hayes | |
| 4,184,453 A | 1/1980 | Ritchey | |
| 4,195,635 A | 4/1980 | Ritchey | |
| 4,209,924 A | 7/1980 | Fearing | |
| 4,250,643 A | 2/1981 | Mackenzie | |
| 4,281,657 A | 8/1981 | Ritchey | |
| 4,359,015 A | 11/1982 | Ritchey | |
| 4,365,436 A | 12/1982 | Ritchey | |
| 4,366,777 A | 1/1983 | Akhavein et al. | |
| 4,368,735 A | 1/1983 | Filmer | |
| 4,402,320 A | 9/1983 | Filmer | |
| 4,425,874 A | 1/1984 | Child | |
| 4,428,327 A | 1/1984 | Steckel | |
| 4,471,546 A | 9/1984 | Bolling, Jr. | |
| 4,497,321 A | 2/1985 | Fearing et al. | |
| 4,506,630 A | 3/1985 | Hair | |
| RE31,940 E | 7/1985 | Ritchey | |
| 4,552,147 A | 11/1985 | Gardner | |
| 4,581,834 A | 4/1986 | Zatkos et al. | |
| 4,597,208 A | 7/1986 | Chevillot | |
| 4,633,606 A | 1/1987 | Cohr | |
| 4,672,966 A | 6/1987 | Haas, Jr. | |
| 4,694,781 A | 9/1987 | Howe et al. | |
| 4,718,697 A | 1/1988 | Berardus van Amelsfort | |
| 4,741,117 A | 5/1988 | Fearing | |
| D296,943 S | 7/1988 | Gardner | |
| 4,819,639 A | 4/1989 | Gardner | |
| 4,878,456 A | 11/1989 | Howe | |
| 4,920,671 A | 5/1990 | Zatkos | |
| 4,931,788 A | 6/1990 | Creswick | |
| 4,953,313 A | 9/1990 | Scott | |
| 4,958,452 A | 9/1990 | Tate | |
| 5,228,224 A | 7/1993 | Gardner | |
| 5,308,351 A | 5/1994 | Nehls | |
| 5,357,700 A | 10/1994 | Schulte | |
| 5,461,807 A | 10/1995 | Johnson | |
| 5,462,554 A | 10/1995 | Gardner | |
| 5,473,830 A | 12/1995 | Doble | |
| 5,482,008 A | 1/1996 | Stafford et al. | |
| 5,588,575 A | 12/1996 | Davignon | |
| 5,615,690 A * | 4/1997 | Giurtino et al. | 600/567 |
| 5,643,284 A | 7/1997 | Hicks | |
| 5,667,515 A | 9/1997 | Chu | |
| 5,768,813 A | 6/1998 | Reboul et al. | |
| 6,007,547 A | 12/1999 | Ritchey | |
| 6,007,548 A * | 12/1999 | Ritchey | 606/117 |
| 6,055,752 A | 5/2000 | Ritchey | |
| 6,145,225 A | 11/2000 | Ritchey | |
| 6,581,262 B1 * | 6/2003 | Myers | 29/268 |
| 6,968,639 B2 | 11/2005 | Destoumieux | |
| 7,441,354 B2 | 10/2008 | Ritchey | |
| 2006/0260156 A1 | 11/2006 | Ritchey | |

FOREIGN PATENT DOCUMENTS

| | | |
|---|---|---|
| CH | 154081 | 4/1932 |
| DE | 29702906 | 4/1997 |
| EP | 0004221 | 9/1979 |
| EP | 0014584 | 8/1980 |
| EP | 0044769 | 1/1982 |
| EP | 0407853 | 1/1991 |
| EP | 1060662 | 12/2000 |
| EP | 1757185 | 2/2007 |
| FR | 2218824 | 9/1974 |
| FR | 2509960 | 1/1983 |
| FR | 2768836 | 3/1999 |
| GB | 1097874 | 1/1968 |
| GB | 1187313 | 4/1970 |
| GB | 2002696 | 2/1979 |
| GB | 2114045 | 8/1983 |
| GB | 2125343 | 3/1984 |
| GB | 2128938 | 5/1984 |
| GB | 0002597 | 3/2003 |
| WO | WO 91/10982 | 7/1991 |
| WO | WO 92/02127 | 2/1992 |
| WO | WO 92/20221 | 11/1992 |
| WO | WO 97/02739 | 1/1997 |
| WO | WO 02/39810 | 5/2002 |
| WO | WO 02/078431 | 10/2002 |
| WO | WO 2007/013820 | 2/2007 |

OTHER PUBLICATIONS

Hasco Tag Company; page of website http://www.hascotag.com/livestock.asp; printed Feb. 4, 2005; 1 page.

U.S. Appl. No. 13/094,199, filed Apr. 26, 2011, Ritchey et al.

* cited by examiner

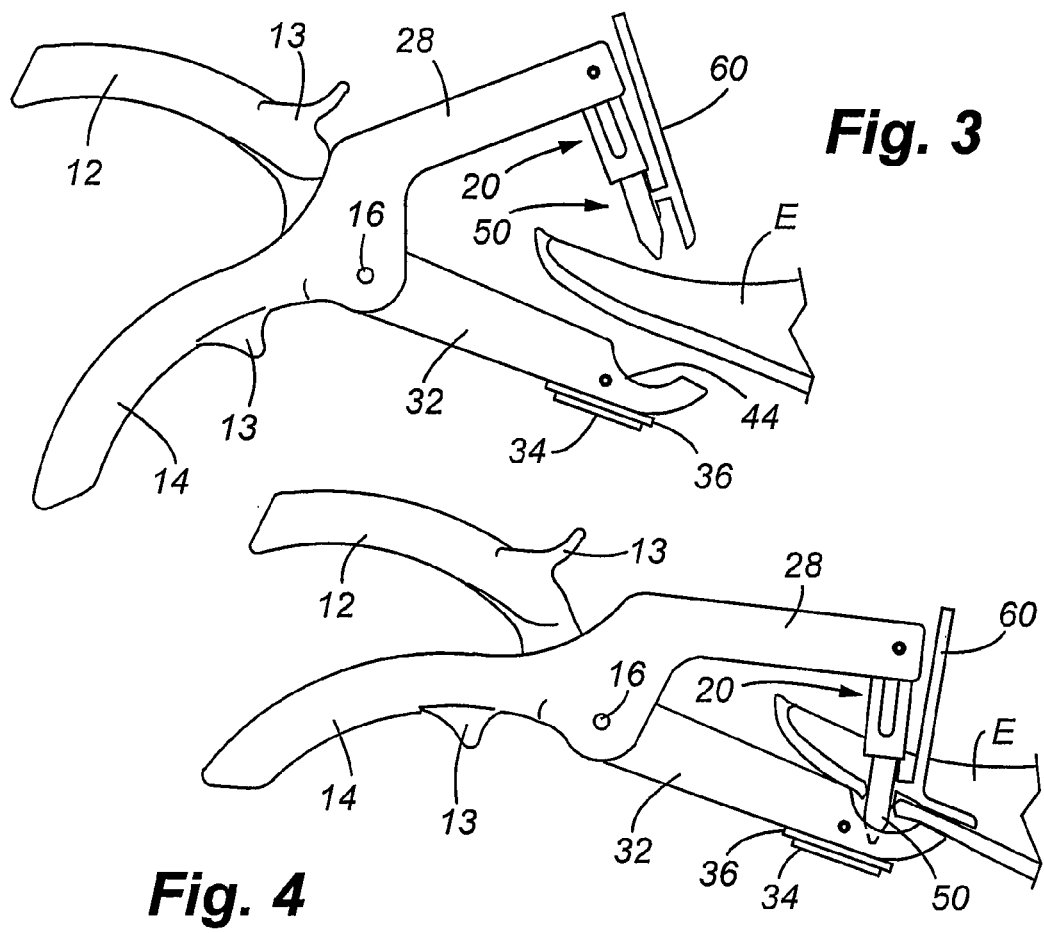
*Fig. 3*
*Fig. 4*
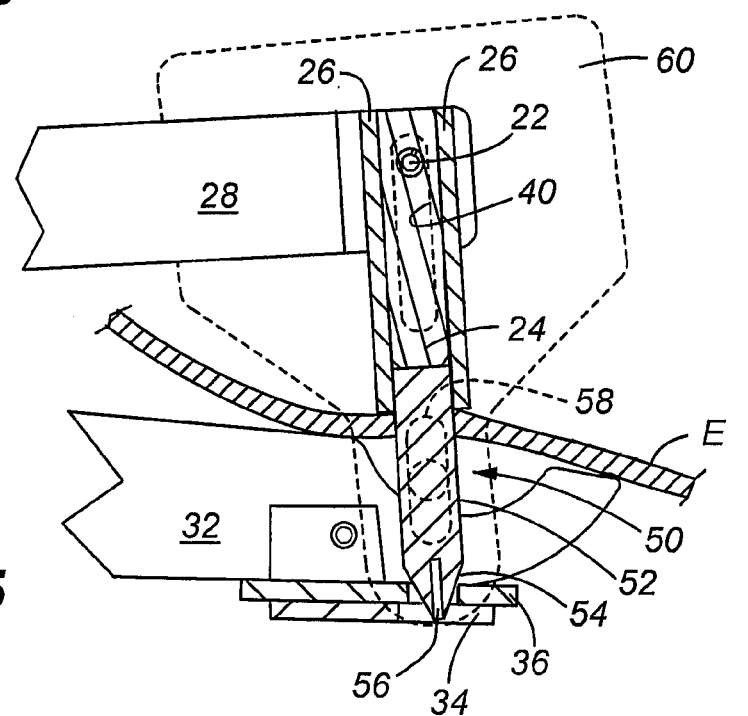
*Fig. 5*

US 8,398,652 B2

EAR TAG INSTALLATION TOOL AND METHOD

FIELD OF THE INVENTION

This invention relates to devices and methods of installing ear tags, and more particularly, to ear tag installation tools and methods for attaching tags to livestock. The tool incorporates a tissue capture feature for obtaining a tissue sample of the tagged animal that can be used for later regulatory testing.

BACKGROUND OF THE INVENTION

A considerable number of prior art devices exist that disclose various types of livestock tag installation tools. One consideration addressed by the prior art devices is to provide reliable and efficient means to install a tag with minimal damage to the animal's ear. Another consideration addressed in the prior art is the provision of an ear tag that will remain securely fastened to the animal throughout its life.

Regulatory schemes in many countries now require increased frequency and scope of testing of the animals for public safety purposes. During the life of an animal, it may be necessary to periodically test the animal for various health issues and to comply with regulations requiring the testing of animal tissue samples.

One group of prior art references that disclose ear tag applicators having a configuration, such as a hand tool with pivotal handles include a number of patents to Gardner. U.S. Pat. No. 4,819,639 to Gardner discloses an ear tag applicator comprising two pivotally connected handle members that are moved between open and closed positions to install the ear tag. One of the handles includes a pivotal bar with the tag attached thereto. The other handle stabilizes the ear and enables the tag to be placed through the ear by closing the handle members. U.S. Pat. Nos. 4,552,147 and 5,462,554 to Gardner also disclose tag applicators having pivotally connected handle members and a pivotal bar for mounting the ear tag. U.S. Pat. No. 5,228,224 to Gardner further discloses an example of an ear tag that may be installed by one or more of the previous Gardner patents.

U.S. Pat. No. 4,368,735 to Filmer is another example of a prior art reference disclosing pivotal handle members and an ear piercing pin or bar.

The Applicant's prior U.S. Pat. No. 6,007,548 discloses an apparatus and method for installing an ear tag. The apparatus includes a pair of handle members, including an inserting member that has attached to it a portion of the tag to be installed. The inserting member penetrates the ear and facilitates mounting of the ear tag by positioning a securing or anchoring tab of the ear tag on the opposite side of the animal's ear. The inserting member is removable and disposable after each use.

While the foregoing inventions are suitable for their intended purposes, there is still a need to provide a livestock tag installation tool which is easy to use, reliable, and prevents cross-contamination between livestock by use of a disposable piercing needle. Repeated use of the same piercing needle between livestock can result in the spreading of disease and other pathogens between the livestock. Therefore, one objective of the present invention is to provide a disposable piercing needle for each use of the device.

Another object of the invention is to provide an ear tag installation tool that quickly and efficiently installs ear tags.

It is another object of the invention to provide a method of installation wherein the livestock tag is reliably secured to the animal with minimal damage to the animal's tissue.

It is yet another object of the invention to provide an ear tag installation tool that incorporates a tissue capture feature in which a tissue sample of the animal may be obtained through a disposable piercing needle that remains secured to the installation tool after use.

It is yet another object of the invention to provide a method for quickly and efficiently obtaining a tissue sample of the animal that does not require the tissue sample to be stored or otherwise made a part of the livestock tag. Accordingly, the tag may be kept intact after installation and yet a tissue sample can be obtained by the piercing needle that remains with the tool as opposed to the needle becoming part of the tag.

SUMMARY OF THE INVENTION

An apparatus and method of installing livestock tags are provided. In a preferred embodiment, the apparatus includes a pair of pivotal handle members used in conjunction with a disposal piercing needle that is attached to a pivoting head on one of the handle members. The piercing needle includes a cutting element or cutting tip that pierces the ear of the animal. A tab portion of the ear tag is removeably connected to the piercing needle. The distal ends of the handle members are placed on opposite sides of the animal's ear and are closed upon one another causing the piercing needle to pass through the ear along with the tab portion of the ear tag. The tab portion is stripped away from the piercing needle after the piercing needle fully penetrates the ear. The piercing needle is ejected from the pivoting head of the handle member and is resiliently held within a needle holder attached to the distal end of the opposing handle member. The tab portion of the tag remains on the opposite side of the ear thereby securing the tag to the ear. The handle members are opened and the next tag can be installed by securing another piercing needle with another tag to the pivoting head of the handle member.

The piercing needle may be especially constructed to include a small distal cavity or bore to form a tissue capture element. The bore is aligned with the angle at which the needle penetrates the ear resulting in a slug of tissue being captured within the bore as the needle passes through the ear. This tissue may then be used for testing purposes, according to regulatory requirements.

The rotating or pivoting head is used to mount the piercing needle. The pivoting head includes a core and a sleeve slidably mounted over the core. In an extended position, the sleeve extends beyond the core and the internal chamber of the sleeve receives the proximal end of the needle. As the needle passes through the animal's ear, and as the distal tip of the piercing needle frictionally slides into the needle holder, the sleeve makes contact with the ear of the animal thereby sliding the sleeve to the retracted position. In the retracted position, the core extends beyond the end of the sleeve thereby exposing the proximal end of the needle and effectively ejecting the needle from within the chamber of the sleeve.

Other features and advantages of the invention will become apparent from a review of the following description, taken in conjunction with the accompanying drawings.

BRIEF DESCRIPTION OF THE DRAWINGS

FIG. 3 is a side view of the installation tool, illustrating a piercing needle secured to the pivoting head, along with a livestock tag mounted to the needle, the handle members shown in the open position, and an ear of an animal positioned for receiving the tag;

FIG. 4 is a side view of the installation tool, illustrating the handle members moved towards the closed position in which the distal tip of the piercing needle passes through the animals ear and into frictional engagement with the needle holder located adjacent the distal end of the other handle member;

FIG. 5 is an enlarged fragmentary cross-sectional view illustrating the position of the tool in FIG. 4;

DETAILED DESCRIPTION

Figure 1:
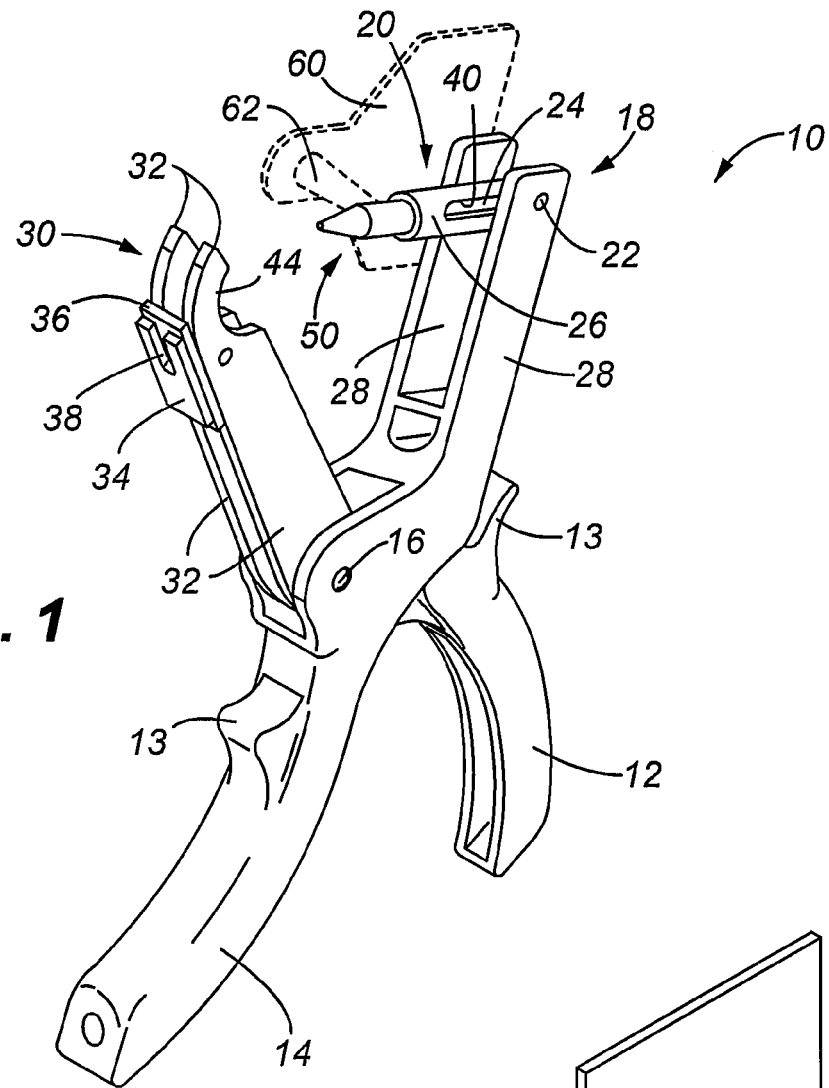
FIG. 1 is a perspective view of a preferred embodiment of the livestock tag installation tool of the present invention.

FIG. 1 illustrates a livestock tag installation tool 10 according to a preferred embodiment. The installation tool 10 is characterized by a first handle member 12 pivotally connected to a second handle member 14 by pin 16. Optional finger grips 13 may be incorporated on the handles to facilitate comfortable positioning of the fingers and to help prevent slippage of the hand when the tool is in use. The distal end 18 of handle member 14 includes a pivoting head assembly 20. The distal end 30 of the opposing handle member 12 includes a flexible needle holder 36, and a base plate 34 that secures the needle holder 36 to the handle member. The needle holder has an opening 38 sized to frictionally receive a piercing needle 50 and to hold the piercing needle 50 once the handler members are closed, as explained below. The needle holder may be a resilient piece of material, such as rubber or plastic. The base plate 34 is preferably rigid to provide support to the needle holder 36, and has a larger opening aligned with the opening 38 of the needle holder.

The distal portion or end 18 of the handle member 14 comprises a pair of spaced forks or tines 28. As shown, the tines 28 extend substantially parallel to one another. Similarly, the distal end or portion 30 of handle member 12 comprises a corresponding pair of tines or spaced prongs 32. The prongs 32 have a curved recess 44 that may facilitate placement of the animal's ear between the distal ends 18 and 30 of the handle members 12 and 14 and for otherwise assisting in holding the portion of the ear to receive the tag. The spaced area between the tines 28 and the curved recess 44 serve to create a cradle or cup that helps to stabilize the ear to prevent the ear from shifting during installation of the tag that could otherwise result in tearing of the ear tissue.

Figure 6:
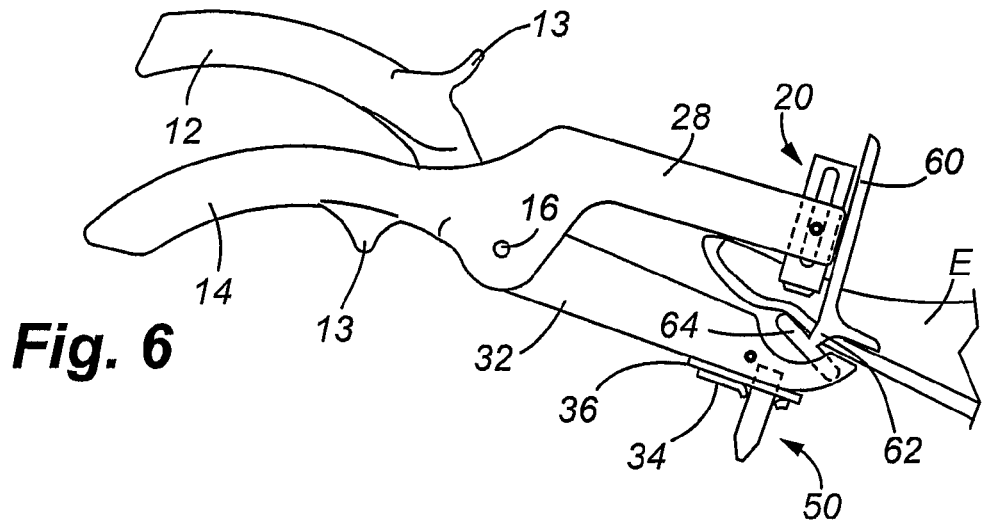
FIG. 6 is another side view of the installation tool, illustrating the piercing needle fully inserted into the needle holder and separated from the pivoting head. At this stage in the installation method, the tab portion of the tag is separated from the needle.
Figure 7:
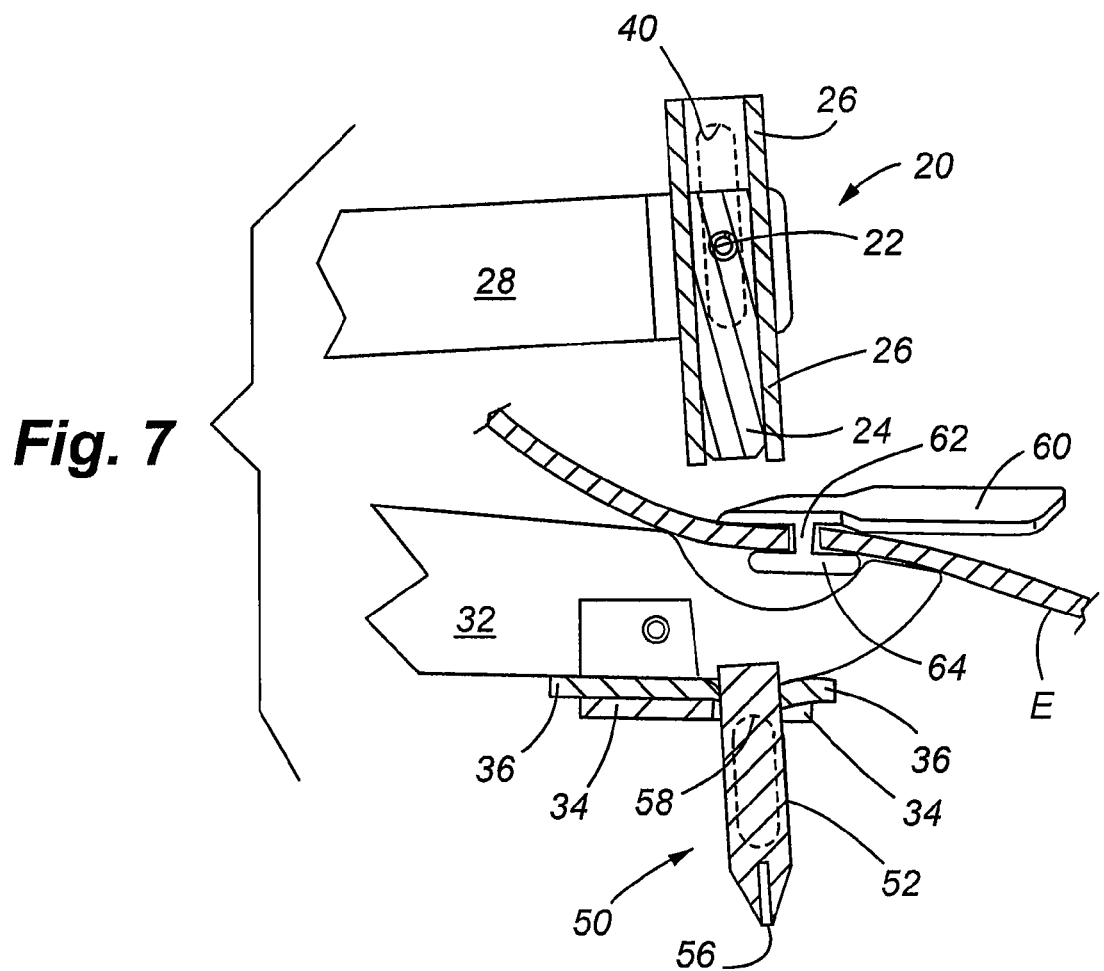
FIG. 7 is an enlarged fragmentary cross-sectional view illustrating the position of the tool in FIG. 6.

The pivoting head assembly 20 is mounted between the tines 28 and is pivotally secured by pin 22. The head assembly may rotate about pin 22 to align the needle 50 at the most optimum angle to penetrate the ear of the animal. A degree of frictional resistance is incorporated with the pin so that the head assembly does not freely rotate, but can be manually adjusted to achieve the desired alignment for the needle. The head assembly 20 includes a core 24 and a slidable sleeve 26 which is slidable over the core 24 between an extended position, such as shown in FIG. 1, and a retracted position, such as shown in FIGS. 6 and 7, as discussed below. The sleeve 26 has a slot 40 that enables the sleeve to slide over the core 24 between the extended position and retracted position. The core 24 is mounted to the pin 22, and therefore can also rotate.

Figure 2:
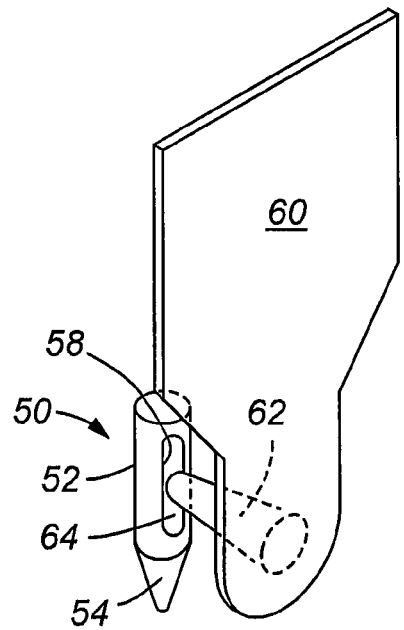
FIG. 2 is a perspective view of the piercing needle showing one type of livestock tag secured to the needle.

Referring also to FIG. 2, the piercing needle 50 is shown with an exemplary livestock tag that is mounted to the needle 50. The livestock tag includes a tag panel 60, a tab 64, and a flexible neck 62 interconnecting the tab 64 to the panel 60. The needle 50 has a body 52 and pointed distal tip 54. The tab 64 is placed within a longitudinal or side groove 58 formed on the body 52 of the needle 50. As shown, the groove extends in the longitudinal or lengthwise direction of the needle 50. The needle 50 may be rotated in any desired orientation when connected to the pivoting head so long as the panel 60 does not interfere with the closing of the handle members. FIG. 1 shows the tag rotated to the lateral side of the tool 10, while the other figures show the tag aligned with the distal end of the tool 10, both positions being suitable for installing the tag without interfering with the closing of the handle members.

Referring to FIG. 3, the animal's ear E is placed between the handle members 12 and 14. As shown in FIGS. 4 and 5, the handle members are moved to the closed position so that the distal tip 54 of the piercing needle 50 passes through the tissue of the ear E, and begins to travel within the flexible needle holder 36. As shown in FIG. 5, the piercing needle 50 includes an optional distal cavity or orifice 56 which is aligned longitudinally with the long axis of the piercing needle. A slug of tissue is captured within the cavity 56 as the needle 50 passes through the animal's ear.

Referring to FIGS. 6 and 7, as the handle members are further closed upon one another, the needle 50 continues to pass through the needle holder 36 and base plate 34, and the sleeve 26 slides to its retracted position in response to the sleeve 26 making contact with the ear E and as the needle 50 is frictionally engaged with the holder 36. The needle 50 is ultimately ejected from within the chamber of the sleeve 26 when the sleeve 26 is in the retracted position.

As the needle 50 enters the needle holder 36, the tab 64 of the tag is stripped away from the groove 58 in the needle, thereby positioning the tab 64 to anchor the tag to the ear E. The neck 62 of the tag passes through the opening formed in the ear E by the piercing needle 50.

Figure 8:
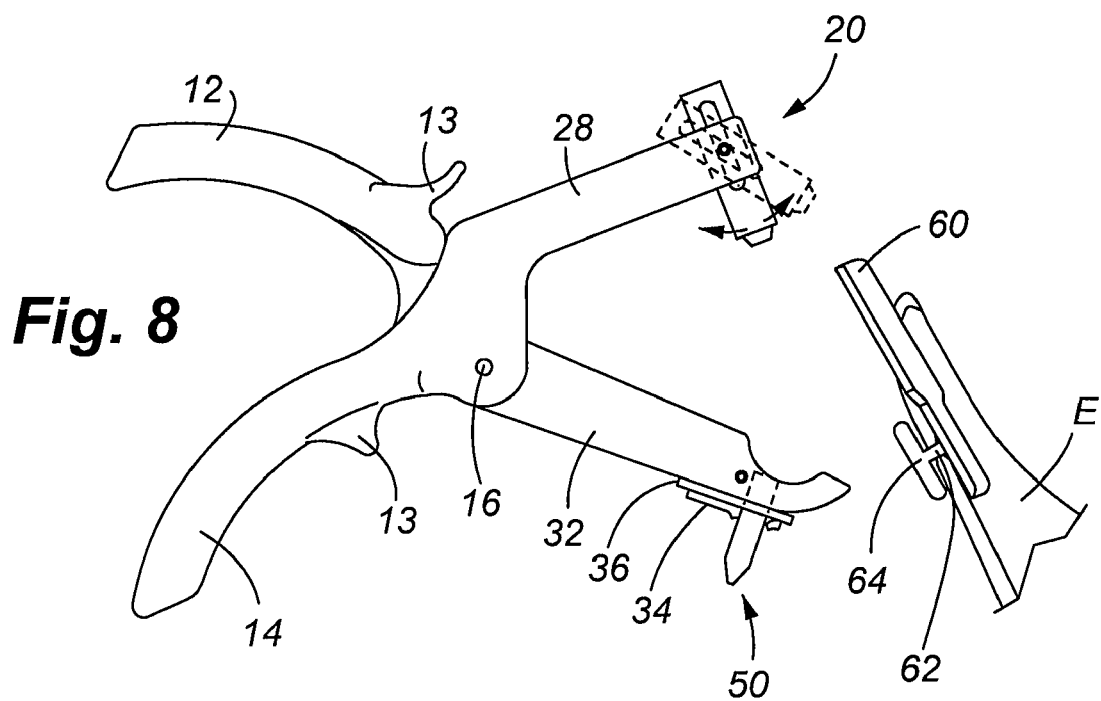
FIG. 8 is another side view showing the needle captured in the needle holder, the sleeve fully retracted, and the handle members moved back to the open position and the tool removed from the animal in preparation for receiving another piercing needle for the installation of the next tag.

As illustrated in FIG. 8, when the ear tag is completely separated from the installation tool 10, the piercing needle 50 is secured to the flexible needle holder 36, and the user may then retrieve the needle 50 in order to process the tissue sample wedged in the distal orifice 56 of the needle. FIG. 8 also shows the ability of the head assembly 20 to rotate about the pin 22 in response to forces that may be applied against the head assembly. For example, if the animal moves its head away from the tool after the tag is attached but before user can clear the tool from the animal, the force of the animal's ear or the installed tag making contact with the head assembly may cause the head assembly to rotate. This rotation by the head assembly helps to prevent the head assembly from damaging the tag and the animal's ear, which otherwise may occur if the animal's ear remains trapped between the handle members. As shown, the head assembly can rotate in either direction to facilitate clearing the tool from the animal after the tag is installed.

To install another ear tag, the sleeve 26 is manually slid back to the extended position, another piercing needle 50 is placed in the cylindrical chamber within the sleeve 26, and another tag is secured to the needle.

The method of installing an ear tag in the ear of the animal is illustrated in the figures. Although the figures illustrate a specific type of ear tag in which the tag has a portion attached to the needle, it should be understood that other types of ear tags can be installed with the tool. For example, the needle could have a circumferential slot that receives a circular shaped tab of the tag placed in the slot.

One advantage of the invention is that the needle can be retrieved with a tissue sample in the needle. In some prior art devices, the needle is incorporated as part of the tag. In the present case, it is an advantage to not make the needle a part of the tag since the tag would have to be removed from the animal in order to retrieve the tissue sample.

The invention has been, described with respect to a preferred apparatus embodiment to include a preferred embodiment for a method of installing a tag. Although the preferred apparatus embodiment illustrates specific structural features, it shall be understood that the invention can be modified commensurate with the scope of the claims appended hereto.

The invention claimed is:

1. An ear tag installation tool, comprising:
a first handle member having proximal and distal ends;
a second handle member having proximal and distal ends, and pivotally connected to the first handle member so that the handle members are movable between an open position, in which the distal ends are spaced apart, and a closed position in which the distal ends are moved toward one another;
a head pivotally connected to the distal end of the second handle member by a pin, the head comprising a core having a distal end, and a cylindrical slidable sleeve positioned over the core and slidable between an extended position and a refracted position, the sleeve having an interior chamber defined by the cylindrical sleeve, the head rotating about the pin during installation of the tag;
a piercing needle having a proximal end received in the chamber of the sleeve and abutting the distal end of the core, and a distal tip including a cutting edge, the needle further having a slot formed on an exterior surface thereof;
a flexible needle holder having an opening and secured to the distal end of the first handle member; and
wherein an ear tag is installed on an ear by inserting a first portion of the ear tag in the slot of the piercing needle, positioning the ear between the distal ends of the handle members while the handle members are in the open position, moving the handle members toward one another so that the piercing needle pierces the ear and causing the slidable sleeve to slide over the core as the distal end of the core moves the needle through the interior chamber of the sleeve and separates the needle from the core.

2. A tool, as claimed in claim 1, further including:
respective finger grips formed on the proximal ends of the handle members to enhance gripping of the handle members.

3. A tool, as claimed in claim 1, wherein:
the needle holder has an opening sized to frictionally receive the piercing needle and to retain the piercing needle after the needle pierces the ear.

4. A tool, as claimed in claim 1, wherein:
the needle holder is made of a flexible material.

5. A tool, as claimed in claim 1, further including:
a base plate secured to the needle holder for stabilizing the needle holder against the distal end of the first handle member.

6. A tool, as claimed in claim 1, wherein:
the distal end of the second handle member comprises a pair of spaced tines extending substantially parallel to one another, and the head being positioned in a gap between the pair of tines, and pivoting about a pin extending transversely and interconnecting the pair of tines.

7. A tool, as claimed in claim 1, wherein:
the distal end of the first handle member comprises a pair of tines spaced apart from one another and extending substantially parallel to one another.

8. A tool, as claimed in claim 1, wherein:
the distal end of the first handle member has a curved recess facing the second handle member.

9. A device as claimed in claim 1, wherein:
the distal end of the piercing needle includes a longitudinally extending cavity to receive and hold a tissue sample of the ear as the piercing needle penetrates the ear of an animal.

10. A tool, as claimed in claim 1, wherein:
the piercing needle has a cylindrical-shaped body, and a converging distal tip forming the cutting edge.

11. An ear tag installation tool comprising:
a first handle member having proximal and distal ends;
a second handle member having proximal and distal ends, and connected to the first handle member so that the handle members are movable between an open position in which the distal ends are spaced apart, and a closed position in which the distal ends are moved toward one another;
a head assembly connected to the second handle member by a pin, the head assembly comprising a core and a cylindrical sleeve positioned over the core and slidable between an extended position and a retracted position, the head assembly rotating about the pin during installation;
a piercing needle secured to the head assembly within a chamber of the cylindrical sleeve defined by the cylindrical sleeve, the needle having a distal tip including a cutting edge and cavity formed in the distal tip to capture tissue of an ear as the needle passes through the ear;
a needle holder having an opening and secured to the first handle member; and
wherein an ear tag is installed on the ear by attaching a first portion of the ear tag to the needle, positioning the ear between the distal ends of the handle members while the handle members are in the open position, moving the handle members toward one another so that the piercing needle pierces the ear, and the core causing the slidable sleeve to slide over the core as a distal end of the core moves the needle through the interior chamber of the sleeve and separates the needle from the core.

* * * * *

UNITED STATES PATENT AND TRADEMARK OFFICE
CERTIFICATE OF CORRECTION

PATENT NO. : 8,398,652 B2
APPLICATION NO. : 12/770320
DATED : March 19, 2013
INVENTOR(S) : Eugene R. Ritchey et al.

It is certified that error appears in the above-identified patent and that said Letters Patent is hereby corrected as shown below:

In the Claims:

At Column 5, line 29 of claim 1, please replace the word "refracted" with the word "retracted".

Signed and Sealed this
Eighteenth Day of June, 2013

Teresa Stanek Rea
*Acting Director of the United States Patent and Trademark Office*